(12) United States Patent
Gale

(10) Patent No.: US 7,622,136 B2
(45) Date of Patent: Nov. 24, 2009

(54) TRANSPARENT TRANSDERMAL NICOTINE DELIVERY DEVICES

(75) Inventor: Robert M. Gale, Los Altos, CA (US)

(73) Assignee: ALZA Corporation, Mountain View, CA (US)

(*) Notice: Subject to any disclaimer, the term of this patent is extended or adjusted under 35 U.S.C. 154(b) by 60 days.

(21) Appl. No.: 10/871,458

(22) Filed: Jun. 18, 2004

(65) Prior Publication Data

US 2004/0234585 A1 Nov. 25, 2004

Related U.S. Application Data

(63) Continuation of application No. 09/464,305, filed on Dec. 15, 1999, now abandoned.

(60) Provisional application No. 60/126,798, filed on Mar. 30, 1999, provisional application No. 60/124,679, filed on Mar. 16, 1999, provisional application No. 60/112,730, filed on Dec. 18, 1998.

(51) Int. Cl.
*A61F 13/00* (2006.01)
*A61F 13/02* (2006.01)

(52) U.S. Cl. .................... 424/449; 424/448; 424/443

(58) Field of Classification Search .............. 424/449, 424/448, 443
See application file for complete search history.

(56) References Cited

U.S. PATENT DOCUMENTS

| | | |
|---|---|---|
| 3,598,122 A | 8/1971 | Zaffaroni |
| 3,598,123 A | 8/1971 | Zaffaroni |
| 3,731,683 A | 5/1973 | Zaffaroni |
| 3,797,494 A | 3/1974 | Zaffaroni |
| 4,031,894 A | 6/1977 | Urquhart et al. |
| 4,144,317 A | 3/1979 | Higuchi et al. |
| 4,201,211 A | 5/1980 | Chandrasekaran et al. |
| 4,286,592 A | 9/1981 | Chandrasekaran |
| 4,314,557 A | 2/1982 | Chandrasekaran |
| 4,379,454 A | 4/1983 | Campbell et al. |
| 4,435,180 A | 3/1984 | Leeper |
| 4,559,222 A | 12/1985 | Enscore et al. |
| 4,568,343 A | 2/1986 | Leeper et al. |
| 4,573,995 A | 3/1986 | Cheng et al. |
| 4,588,580 A | 5/1986 | Gale et al. |
| 4,597,961 A | 7/1986 | Etscorn |
| 4,645,502 A | 2/1987 | Gale et al. |
| 4,698,062 A | 10/1987 | Gale et al. |
| 4,704,282 A | 11/1987 | Campbell et al. |
| 4,725,272 A | 2/1988 | Gale |
| 4,758,434 A | 7/1988 | Kydonieus et al. |
| 4,764,382 A | 8/1988 | Kydonieus et al. |
| 4,781,924 A | 11/1988 | Lee et al. |
| 4,788,062 A | 11/1988 | Gale et al. |
| 4,816,258 A | 3/1989 | Nedberge et al. |
| 4,839,174 A | 6/1989 | Baker et al. |
| 4,849,226 A | 7/1989 | Gale |
| 4,904,475 A | 2/1990 | Gale et al. |
| 4,908,027 A | 3/1990 | Enscore et al. |
| 4,908,213 A | 3/1990 | Govil et al. |
| 4,915,950 A | 4/1990 | Miranda et al. |
| 4,917,895 A | 4/1990 | Lee et al. |
| 4,938,759 A | 7/1990 | Enscore et al. |
| 4,943,435 A | 7/1990 | Baker et al. |
| 4,946,853 A | 8/1990 | Bannon et al. |
| 5,004,610 A | 4/1991 | Osborne et al. |
| 5,016,652 A | 5/1991 | Rose et al. |
| 5,071,656 A | 12/1991 | Lee et al. |
| 5,077,104 A | 12/1991 | Hunt et al. |
| 5,122,382 A | 6/1992 | Gale et al. |
| 5,141,750 A | 8/1992 | Lee et al. |
| 5,167,649 A | 12/1992 | Zook |
| 5,230,896 A | 7/1993 | Yeh et al. |
| 5,284,660 A | 2/1994 | Lee et al. |
| 5,314,694 A | 5/1994 | Gale et al. |
| 5,342,623 A | 8/1994 | Enscore et al. |
| 5,364,630 A | 11/1994 | Osborne et al. |
| 5,372,819 A * | 12/1994 | Godbey et al. .............. 424/449 |
| 5,411,739 A | 5/1995 | Jaeger et al. |
| 5,411,740 A | 5/1995 | Lee et al. |
| 5,462,745 A | 10/1995 | Enscore et al. |
| 5,508,038 A | 4/1996 | Wang et al. |
| 5,599,554 A | 2/1997 | Majeti |
| 5,603,947 A | 2/1997 | Wong et al. |
| 5,626,866 A | 5/1997 | Ebert et al. |
| 5,635,203 A | 6/1997 | Gale et al. |
| 5,726,190 A | 3/1998 | Rose et al. |
| 5,976,565 A * | 11/1999 | Fotinos ....................... 424/448 |
| 6,010,715 A | 1/2000 | Wick et al. |
| 6,203,817 B1 | 3/2001 | Cormier et al. |
| 6,512,010 B1 | 1/2003 | Gale et al. |
| 6,562,363 B1 * | 5/2003 | Mantelle et al. ............. 424/434 |
| 2008/0031933 A1 | 2/2008 | Gale |

FOREIGN PATENT DOCUMENTS

| | | |
|---|---|---|
| CA | 2250025 | 10/1997 |
| EP | 0 563 507 A1 | 10/1993 |
| JP | 60069014 | 4/1985 |
| JP | 07165563 A * | 6/1995 |
| WO | WO 97/33581 A1 | 9/1997 |

OTHER PUBLICATIONS

The article "Drug patches catch on", chembytes e-zine, Oct. 1995.*

(Continued)

*Primary Examiner*—Isis A Ghali
(74) *Attorney, Agent, or Firm*—Stoel Rives LLP; Samuel E. Webb; Matthew S. Bethards

(57) ABSTRACT

A transparent transdermal delivery device for delivering nicotine which has an Opacity Index of less than 48.6%.

12 Claims, No Drawings

OTHER PUBLICATIONS

U.S. Appl. No. 09/464,305, Dec. 15, 1999, Gale.
"Clear NicoDerm CQ Now Available in US", Doctor's Guide. http://www.plsgroup.com, 2000.IG, Aug. 20, 2009.
Office Action dated Feb. 5, 2009 for U.S. Appl. No. 11/841,789.
Office Action dated Jul. 31, 2008 for U.S. Appl. No. 11/841,789.
Office Action dated Mar. 24, 2004 for U.S. Appl. No. 09/464,305.
Office Action dated Feb. 26, 2002 for U.S. Appl. No. 09/464,305.
Office Action dated Jul. 12, 2001 for U.S. Appl. No. 09/464,305.
Office Action dated Dec. 14, 2000 for U.S. Appl. No. 09/464,305.
Office Action dated Jun. 12, 2000 for U.S. Appl. No. 09/464,305.
Office Action dated Aug. 19, 2009 for U.S. Appl. No. 11/841,789.
Wang et al., "Surface Nature of UV Deterioration in Properties of Solid Poly (ethylene terephthalate)." Journal of Applied Polymer Science, vol. 67, pp. 705-714 (1998).
US 5,344,646, 09/1994, Enscore (withdrawn)

* cited by examiner

TRANSPARENT TRANSDERMAL NICOTINE DELIVERY DEVICES

CLAIM OF PRIORITY

This application is a continuation of U.S. Ser. No. 09/464,305, filed Dec. 15, 1999 which now abandoned, claims the benefit of U.S. provisional patent applications Ser. No. 60/112,730, filed Dec. 18, 1998; 60/124,679, filed Mar. 16, 1999; and 60/126,798, filed Mar. 30, 1999, all of which are incorporated herein by reference.

FIELD OF THE INVENTION

The present invention relates to transdermal delivery devices for administering nicotine for use in smoking cessation treatments. In particular, the invention is directed to transdermal nicotine delivery devices which are transparent.

BACKGROUND OF THE INVENTION

The transdermal route of parenteral drug delivery provides many advantages over other administration routes. Transdermal systems for delivering a wide variety of drugs or other beneficial agents are described in U.S. Pat. Nos. 3,598,122; 3,598,123; 3,731,683; 3,797,494; 4,031,894; 4,144,317; 4,201,211; 4,286,592; 4,314,557; 4,379,454; 4,435,180; 4,559,222; 4,568,343; 4,573,995; 4,588,580; 4,645,502; 4,698,062; 4,704,282; 4,725,272; 4,781,924; 4,788,062; 4,816,258; 4,849,226; 4,904,475; 4,908,027; 4,917,895; 4,938,759; 4,943,435; 5,004,610; 5,071,656; 5,122,382; 5,141,750; 5,284,660; 5,314,694; 5,342,623; 5,411,740; and 5,635,203, which are hereby incorporated in their entirety by reference.

The administration of nicotine buccally, nasally and transdermally to assist a patient desiring to quit smoking has been shown to be clinically effective in reducing the rate of recidivism. Nicotine chewing gum and transdermal nicotine are two of the most widely used forms of nicotine replacement therapy currently available. Transdermal devices for administering nicotine are disclosed in U.S. Pat. Nos. 4,597,961; 4,758,434; 4,764,382; 4,839,174; 4,908,213; 4,915,950; 4,943,435; 4,946,853; 5,004,610; 5,016,652; 5,077,104; 5,230,896; 5,411,739; 5,462,745; 5,508,038; 5,599,554; 5,603,947 and 5,726,190, for example, which are hereby incorporated in their entirety by reference.

Most of the transdermal drug delivery devices of the prior art utilize an impermeable backing on the skin distal surface of the device to protect the device from damage and to prevent loss of the active ingredient(s). In order to improve user satisfaction, these backing layers are often tinted to a color similar to skin tones. However, as can be readily appreciated, it is not commercially practical to provide pigmented backing layers for transdermal systems which approximate all skin colors.

Another approach that has been taken is to provide transparent transdermal systems in which all elements forming a device are sufficiently transparent to permit the natural skin color to be visible through the device. Marketed products which take this approach include the ALORA® and CLIMARA® estrogen replacement patches and the DURAGESIC® transdermal fentanyl delivery system. When these devices are applied to the skin, the patient's natural skin color is visible through the patch, making the presence of the patch extremely inconspicuous. Government regulations require that these products bear identifying indicia, but the indicia can be printed on these devices in light colored or white ink which is not noticeable from a distance of several feet, but is still readable on close inspection.

Such transparent patches have been found useful with non-volatile drugs such as fentanyl and hormone replacement steroids, but no such transparent product has been developed for the delivery of nicotine.

Nicotine is a liquid alkaloid that is colorless, volatile, strongly alkaline, readily oxidized, subject to degradation on exposure to light and highly permeable through not only the human skin, but also many of the polymers conventionally used in the fabrication of backing layers and packaging materials for transdermal products (see for example U.S. Pat. No. 5,077,104). As a result, the backing layers of the transdermal nicotine delivery devices currently available utilize opaque, skin-colored multilaminate films which typically contain a metallized layer, such as aluminum.

Not only do the commercially available transdermal nicotine patches use opaque backings, but many of these devices, due to the complexities of handling and processing nicotine, have other components which are not transparent. For example, the original Prostep® transdermal nicotine product used a drug reservoir in the form of an opaque white gel, held in place by an opaque adhesive overlay. The HABITROL® and NICOTROL® nicotine patches incorporated absorbant pads in the drug reservoir in which the nicotine was absorbed.

It has also been proposed to co-administer nicotine with other substances that improve nicotine cessation therapy. See, for example, U.S. Pat. Nos. 4,908,213; 5,599,554; and 5,726,190 noted above, and WO 97/33581.

SUMMARY OF THE INVENTION

The present invention relates to transparent transdermal delivery devices for the transdermal administration of nicotine, either alone or in combination with other agents.

Such devices should be sufficiently transparent so that the subject's skin can be clearly visible through the device when it is placed on the skin. Identifying indicia can be printed on the device in light colored or white ink in a manner which is not noticeable from a short distance, but is readable on close inspection.

DETAILED DESCRIPTION OF THE INVENTION

Preferred devices of this invention utilize, as the backing layer, a transparent polymeric film which has a permeability to nicotine of less than 1 $\mu g/cm^2 \cdot hr$, preferably less than 0.5 $\mu g/cm^2 \cdot hr$, a solubility for nicotine that is less than 1% by weight and preferably less than 0.1%. Such films are preferably less than about 6 mils thick and most preferably about 2-4 mils thick. Such films are used in combination with one or more of the conventional elements of a transdermal device (other than the removable release liner) such as the drug reservoir, adhesive and rate controlling membranes, which must also be sufficiently transparent as to permit the natural skin color to be clearly visible through the assembled device after placement on the skin. The finished product should have an Opacity Index of less than about 48.6%, preferably less than about 35.11% and more preferably less than 20%.

In addition to being transparent and being sufficiently impermeable to nicotine, the backing layer must also have sufficient mechanical strength and physical integrity to maintain the system intact throughout its intended administration period, which is typically 18-24 hours, and must provide a stable interface with adjoining layers such as the drug reservoir or adhesive layers of the transdermal device. This combination of properties is not always found in one material, and thus the transparent backing layers used on the devices of this invention can be multilaminate films. In addition to having a low permeability to nicotine, a backing layer must also have a low solubility for nicotine. This is because nicotine is toxic and it could be dangerous for a child, for example, to lick the backing layer if it contained a substantial amount of dissolved nicotine.

Suitable polymer materials possessing properties required by this invention include SCOTCHPAK® 1220 film, which is a polyethylene terephthalate/ethylene vinyl acetate (PET EVA), bilaminate film sold by the 3M Company, Minneapolis, Minn. and SARANEX® 2057 film, which is a high density polyethylene (HDPE)/ethylene acrylic acid (EAA)/nylon/EAA multilaminate available from the Dow Chemical Company, Midland, Mich. Nitrile rubber graft copolymers with acrylonitrile and methyl acrylate sold as Barex® films described in U.S. Pat. No. 5,077,104 noted above, can also be used.

These films, comprising a graft copolymer formed from about 73-77% acrylonitrile and from about 23-27% methyl acrylate copolymerized in the presence of about 8-10 parts by weight of butadiene/acrylonitrile copolymers containing approximately 70% by weight of polymer units derived from butadiene are preferred backing materials.

The transparent transdermal delivery devices of this invention can be of any of the forms described in the aforementioned patents. The preferred form, however, comprises a laminate of the backing layer, a nicotine reservoir layer which contains nicotine dissolved in a carrier at a concentration below the saturation concentration of nicotine in the carrier. If the drug reservoir component is self adhesive, a simple monolithic device could be employed. However, in many cases it is desirable to include additional components such as rate controlling membranes, and a separate adhesive layer for maintaining the devices on the skin such as is described in U.S. Pat. Nos. 5,004,610 and 5,342,623 listed above. It is further contemplated that in addition to nicotine, the device may also contain other drugs or other active substances which cooperate with or enhance the effect of nicotine in smoking cessation, smoking replacement or smoking substitution therapy. For all these devices, a removable release liner would normally be applied on the adhesive surface of the patch that is used to keep the device on the skin, which release liner is removed prior to use.

Various materials suited for fabrication of the various components are known in the art and are disclosed in the aforementioned patents.

The adhesive component is preferably a pressure sensitive adhesive including, but not limited to, polysiloxanes, polyacrylates, polyurethanes, acrylic adhesives including cross linked or uncross linked acrylic copolymers, vinyl acetate adhesives, ethylene vinylacetate copolymers, and natural or synthetic rubbers including polybutadienes, polyisoprenes, and polyisobutylene adhesives, and mixtures and graft copolymers thereof. The devices may also be provided with hydrophilic water absorbing polymers known in the art such as polyvinyl alcohol and polyvinyl pyrolidone individually or in combination. The adhesive can be used to form a monolithic delivery device in which the nicotine is dissolved in the adhesive to form a self-adhesive drug reservoir. Alternatively, the adhesive can be applied to the surface of a non-adhesive reservoir in which nicotine is dissolved, to form a multilaminate device. A rate-controlled membrane can also be interfaced between the nicotine reservoir and the adhesive, as is known to the art.

The nicotine can be administered in combination with another agent which could include anti-anxiolytics, antihypertensives, antidepressants, and appetite suppressants, such as fluoxetine, caffeine, buspirone, phenylpropanolamine, clonidine, paroxetine, citalopram, and sertraline.

The nicotine in the device is present in the reservoir at a subsaturated condition (i.e. less than unit activity) such that no undissolved nicotine is present in the reservoir. If other agents are present in the device, they are preferably present fully dissolved, but can be present in undissolved form so long as the end product displays the proper degree of transparency.

In the present invention, nicotine and optionally other agents to be co-administered are delivered through the skin or other body surface at a therapeutically effective rate for a predetermined time period which for nicotine is preferably 16-24 hours.

The transdermal therapeutic devices of the present invention are prepared in a manner known in the art, such as by those procedures described in the transdermal device patents listed previously herein.

The following example is offered to illustrate the practice of the present invention and is not intended to limit the invention in any manner.

EXAMPLE 1

Various commercially available transdermal patches were tested to determine their transparency and compared to the transparent nicotine patches according to this invention. The nicotine patches were prepared as set forth in Example IV of U.S. Pat. No. 5,004,610 with a PET/EVA(SCOTCHPAK® 1220 film, 3M, Minneapolis, Minn.) or SARANEX® film (Dow Chemical Company, Midland, Mich.) backing substituted for the Scotchpak 1006 film backing. The light transmitted through the various systems was measured by a MACBETH 1500/Plus color measurement system (Kollmorgem Instruments Corp., Newburgh, N.Y.). Table 1 shows the Opacity Index, which is the percentage of incidental light which is absorbed by passage through the device, for the various systems tested.

TABLE 1

Patch Opacity

| Patch | Opacity Index |
|---|---|
| MINITRAN ® | 48.6% |
| ALORA ® | 20.21% |
| FEMPATCH ® | 35.11% |
| CLIMARA ® | 19.33% |
| Ex. 1 - Nicotine with SARANEX ® backing | 17.04% |
| Ex. 1 - Nicotine with PET/EVA backing | 19.66% |

The Minitran® nitroglycerine system is clearly visible from a distance of about 5 feet, whereas the FEMPATCH® patch is significantly less noticeable. The ALORA®, CLIMARA® and NICODERM® patches, however, are extremely inconspicuous. Accordingly, transdermal devices according to this invention should have an Opacity Index less than 48.6%, preferably less than 35.11%, more preferably less than 20%.

Having thus generally described our invention and preferred embodiments thereof, it is apparent that various modifications and substitutions will be apparent to workers skilled in the art. These modifications and substitutions can be made without departing from the scope of our invention which is limited only by the following claims.

I claim:

1. A method for making a device for transdermal administration on skin, comprising: providing a backing made from a material selected from the group consisting of PET/EVA laminate, HDPE/EAA/nylon/EAA multilaminate, and film comprising a graft copolymer formed from 73-77% acrylonitrile and 23-27% methyl acrylate copolymerized in the presence of 8 to 10 parts by weight of butadiene/acrylonitrile copolymers; forming a transdermal device with the backing and a nicotine-containing drug reservoir with adhesive for maintaining the device in nicotine transmitting relationship with the skin, such that the device comprising the backing, and the drug reservoir with the adhesive as applied to the skin has a device Opacity Index of less than 48.6% to permit the skin to be visible through the device, wherein the device can be used for 18-24 hour nicotine delivery.

2. The method of claim 1 comprising providing the backing having a nicotine permeability of less than 1.0 µg/cm$^2$hr.

3. The method of claim 1 comprising providing the backing having a nicotine permeability of less than 0.5 µg/cm$^2$ hr.

4. The method of claim 2 comprising providing the backing having a solubility for nicotine of less than 1 wt%.

5. The method of claim 4 comprising providing the backing having a solubility for nicotine of less than 0.1 wt%.

6. The method of claim 1, further comprising providing the backing layer, the drug reservoir and the adhesive such that the Opacity Index of the device is less than 35.11%.

7. The method of claim 6 wherein the Opacity Index of the device is less than 20%.

8. The method of claim 1, further comprising providing the backing from a material selected from the group consisting of PET/EVA laminate, HDPE/EAA/nylon/EAA multilaminate and a film comprising a graft copolymer formed from 73-77% acrylonitrile and from 23-27% methyl acrylate copolymerized in the presence of 8-10 parts by weight of butadiene/acrylonitrile copolymers containing 70% by weight of polymer units derived from butadiene.

9. The method of claim 8 wherein the backing is PET/EVA laminate.

10. The method of claim 8 wherein the backing is HDPE/EAAInylon/EAA multilaminate.

11. The method of claim 8 wherein the backing is a film comprising a graft copolymer formed from 73-77% acrylonitrile and from 23-27% methyl acrylate copolymerized in the presence of about 8-10 parts by weight of butadiene/acrylonitrile copolymers containing 70% by weight of polymer units derived from butadiene.

12. A method for making a device for transdermal administration on skin, comprising: providing a backing having transparency made from a material selected from the group consisting of PET/EVA laminate, HDPE/EAA/nylon/EAA multilaminate, and film comprising a graft copolymer formed from acrylonitrile and methyl acrylate copolymerized in the presence of butadiene/acrylonitrile copolymers; forming a transdermal device with the backing, a nicotine-containing drug reservoir, and adhesive for maintaining the device in nicotine transmitting relationship with the skin, such that the device comprising the backing, drug reservoir, and adhesive as applicable to the skin has a device Opacity Index of less than 48.6% to permit the skin to be visible through the device, wherein the device can be used for 18-24 hour nicotine delivery.

* * * * *